United States Patent [19]
Foster

[11] Patent Number: 5,947,284
[45] Date of Patent: Sep. 7, 1999

[54] PACKAGE WITH GUIDE FOR FLEXIBLE MEDICAL INSTRUMENTS

[75] Inventor: Brian W. Foster, Trumbull, Conn.

[73] Assignee: United States Surgical Corporation

[21] Appl. No.: 09/023,600

[22] Filed: Feb. 13, 1998

[51] Int. Cl.[6] ............ B65D 85/20; B65D 83/10; A61B 19/02
[52] U.S. Cl. .......... 206/364; 206/438; 206/564; 206/571
[58] Field of Search .................. 206/363, 364, 206/564, 571, 438

[56] References Cited

U.S. PATENT DOCUMENTS

| | | | |
|---|---|---|---|
| 3,633,758 | 1/1972 | Morse et al. | 206/364 X |
| 3,750,875 | 8/1973 | Juster | 206/364 |
| 3,802,555 | 4/1974 | Grasty et al. | |
| 4,111,302 | 9/1978 | Roth | 206/363 |
| 4,366,901 | 1/1983 | Short | 206/364 X |
| 4,511,035 | 4/1985 | Alpern | |
| 4,630,729 | 12/1986 | Hirt et al. | |
| 4,811,847 | 3/1989 | Reif et al. | 206/571 |
| 5,031,775 | 7/1991 | Kane | 206/571 |
| 5,284,244 | 2/1994 | O'Toole et al. | |
| 5,323,905 | 6/1994 | Gerondale et al. | |
| 5,353,929 | 10/1994 | Foster | |
| 5,381,896 | 1/1995 | Simons | |
| 5,386,908 | 2/1995 | Sinn | 206/363 |
| 5,392,917 | 2/1995 | Alpern et al. | |
| 5,392,918 | 2/1995 | Harrison | 206/364 X |
| 5,413,217 | 5/1995 | Sauer | |
| 5,415,180 | 5/1995 | Horan | |
| 5,447,230 | 9/1995 | Gerondale | |
| 5,464,025 | 11/1995 | Charles et al. | |
| 5,485,917 | 1/1996 | Early | |
| 5,542,539 | 8/1996 | Early | |

Primary Examiner—Byron P. Gehman

[57] ABSTRACT

A package tray for holding a medical instrument having a resiliently flexible distal end portion improves the control of the distal end during removal of instrument by limiting the withdrawal of the distal end portion of the instrument from an arcuate portion of storage space in the tray to movement in a direction longitudinal with respect to the instrument, thereby preventing side to side whipping motion of the distal end portion upon withdrawal of the instrument from the package.

19 Claims, 5 Drawing Sheets

PACKAGE WITH GUIDE FOR FLEXIBLE MEDICAL INSTRUMENTS

BACKGROUND

1. Technical Field

The present disclosure relates to packages, and particularly to packages for medical instruments.

2. Background of the Art

Various types of packages for medical instruments are known in the art. Typically, such packages, after being hermetically sealed, are impervious to penetration by microbes. Some types of packages have a side fabricated from a sheet of porous, microbe impervious material. Such material allows the package to be sterilized by, for example, steam, ethylene oxide, or radiation, after the medical instrument has been hermetically sealed therein.

For example, U.S. Pat. No. 5,353,929 to Foster discloses a package for an elongated surgical instrument having a handle portion, an elongated portion, and a distal end. The package includes channels for receiving the instrument. Flanges retain the instrument in the channels.

Certain instruments, for example those used in minimally invasive surgery (e.g., laparoscopy, endoscopy, arthroscopy) have elongated distal portions for insertion through a trocar cannula. Some instruments have a flexible distal portion which advantageously permits the distal portion to be curved into an arcuate shape, thereby allowing the instrument to be packaged with greater efficiency and flexibility in the use of storage space. For example, electrosurgical instruments can include a conductive metal wire and sleeve as the distal portion. However, such wires are typically very resilient and biased to a straight configuration. If the instrument is abruptly removed from a package, the distal portion can uncontrollably whip around and contact non-sterile surfaces or possibly operating room personnel.

SUMMARY

A package is provided herein for a medical instrument having a resiliently flexible elongated member defining a longitudinal direction and extending distally from a body portion of the instrument. The package includes a tray with a storage space for holding the medical instrument, the storage space being formed by a depression in the tray and including a narrow arcuate portion for reception of the resiliently flexible elongated member. The package further includes limiting means associated with the tray for limiting the withdrawal of the resiliently flexible elongated member from the narrow arcuate portion of the storage space to movement in a substantially longitudinal direction.

In a preferred embodiment the limiting means includes a flexible guide tube having a bore sized and configured to receive the resiliently flexible elongated member of the medical instrument, the flexible guide tube being engageable within the elongated arcuate portion of the storage space for holding the medical instrument.

Preferably, the elongated portion of the storage space includes at least one curved wall having at least one projection with an undercut for snap fit releasable engagement with the flexible guide tube.

BRIEF DESCRIPTION OF THE DRAWINGS

Various embodiments are described below with reference to the drawings wherein.

DETAILED DESCRIPTION OF PREFERRED EMBODIMENTS

Figure 1:
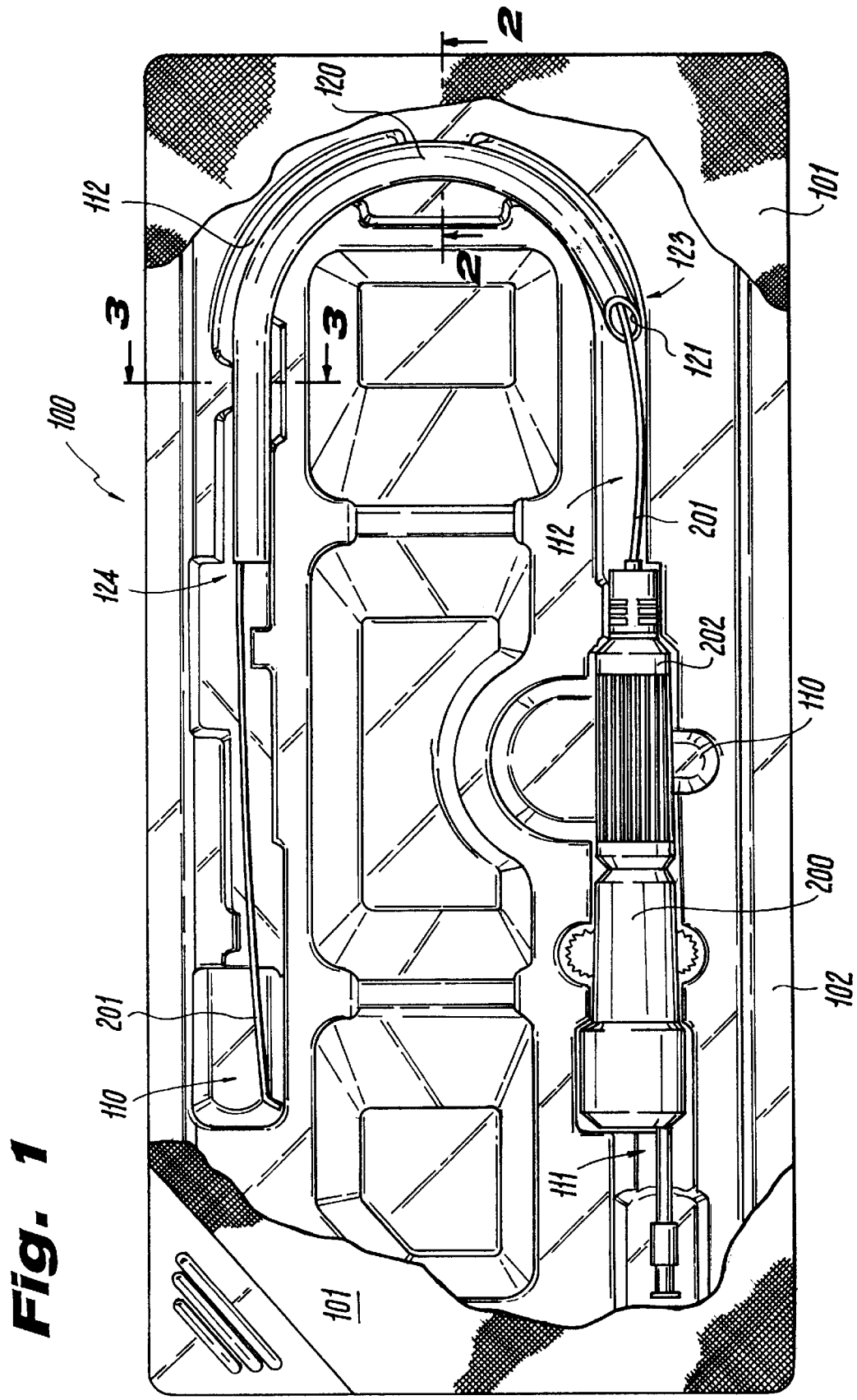
FIG. 1 is cutaway plan view of the surgical instrument package with a surgical instrument stored therein.

Referring to FIG. 1, the medical instrument package 100 includes a cover 101 and a tray 102. The cover 101 is a sheet of microbe impervious material and can be a non-porous material such as metal foil or plastic film, or a porous material such as a sheet of spun bonded polyolefin fiber such as TYVEK® brand sheet. The cover 101 is hermetically sealed to the tray 102 by conventional methods after the medical instrument is inserted in the package. Use of a microbe impervious porous sheet such as TYVEK® brand permits the interior of the package and its contents to be sterilized by gases (e.g., steam, ethylene oxide, and the like) as well as by γ-radiation after the package has been hermetically sealed. Such methods of sterilization are well known in the art.

The tray 102 is preferably thermoformed plastic sheet fabricated from a suitable polymer such as polyethylene terephthalate, polyvinyl chloride, polypropylene, polystyrene, and the like. Preferably, the tray 102 is transparent and may be tinted or clear. Such thermoformed blister packages are fabricated using conventional thermoforming equipment and methods. Typically, in such a process the sheet of plastic is heated to a temperature sufficient to render it pliable. The heated plastic sheet is positioned on a mold having cavities corresponding to the desired structure of the package. A vacuum is drawn through perforations in the mold to configure the plastic sheet into a shape which conforms to the contour of the mold, after which the plastic sheet is cooled to reharden it and is then released from the mold. The thickness of the plastic sheet typically ranges from about 0.01 inches to about 0.06 inches, for example.

The tray 102 at least partially defines an interior instrument storage space which includes one or more cavities 110 into which the medical instruments are inserted.

Instrument 200 can be any instrument having an elongated narrow distal portion 201 which extends from an instrument body 202. For purposes of exemplification, instrument 200 as shown herein is an electrosurgical instrument for the needle ablation of body tissue, particularly the transurethral needle ablation of prostate tissue. Such an instrument is disclosed and described in U.S. patent application Ser. No. 08/699,091 filed Aug. 16, 1996. Distal portion 201 can be, for example, a resiliently flexible elongated member such as a long wire (with or without a plastic coating) and/or metal sleeve, which is both flexible and resilient. The flexibility of distal portion 201 permits it to be curved into an arcuate configuration for more efficient use of storage space in the bottom portion 102. Resiliency gives distal portion 201 a bias towards an unbent configuration.

Cavity 110 into which instrument 200 is placed includes a relatively wide cavity first portion 111 into which the body portion 202 of the instrument 200 is secured, and a relatively narrow and arcuate cavity second portion 112 into which the distal portion 201 is secured.

Tube 120 serves as a withdrawal guide, or guide tube, for the medical instrument 200 and is an elongated, preferably flexible member having a bore 121 for reception therethrough of the distal portion 201 of the instrument. Bore 121 preferably range in diameter of from about 0.06 inches to about 0.312 inches and terminates in first and second end openings 123 and 124. As shown in FIG. 1, first end opening 123 is formed by an angled cut in the tube to facilitate insertion of narrow distal portion 201 therethrough; second opening 124 is optionally formed by a perpendicular (i.e. perpendicular to the axis of the tube,) cut in tube 120. However, either one or both of the first and second end openings 123 and 124 can be formed from angled or perpendicular cuts. Optionally, bore 121 can have a first end 123 opening and be sealed at the other end provided that the length of the tube 120 is sufficient to accept distal portion 201. The outer diameter of tube 120 preferably ranges in diameter from about 0.18 inches to about 0.375 inches. The length of tube 120 preferably ranges from about 10 inches to about 15 inches. Tube 120 is preferably fabricated from a flexible polymeric material such as polyethylene, fluorocarbon polymer (e.g., TEFLON® brand polytetrafluoroethylene), polyvinyl chloride ("PVC"), nylon, or any other material suitable for the purposes described herein. Alternatively, guide tube 120 can be relatively rigid enough to withstand kinking.

Figure 2:
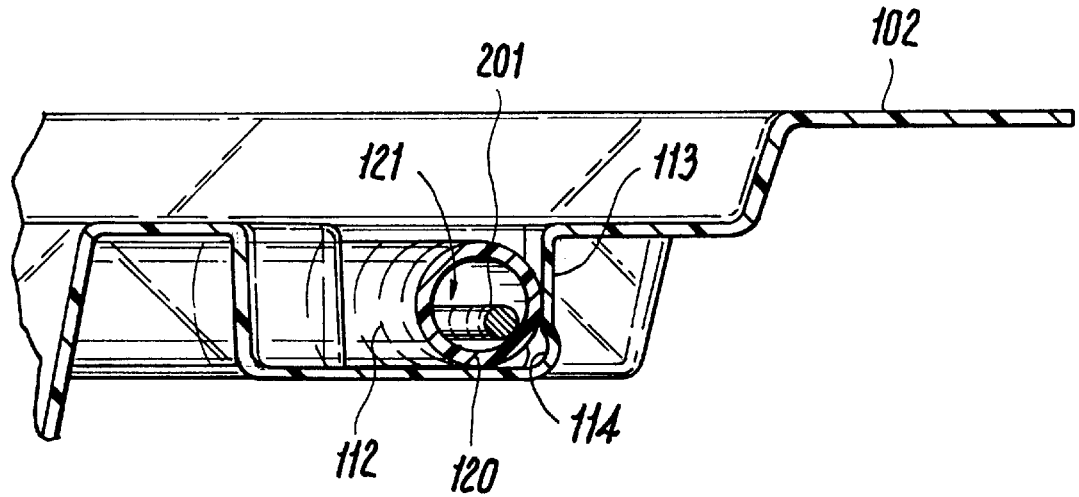
FIGS. 2 and 3 are partly cutaway sectional views of the surgical instrument package with a surgical instrument stored therein taken along lines 2—2 and 3—3, respectively, in FIG. 1.
Figure 3:
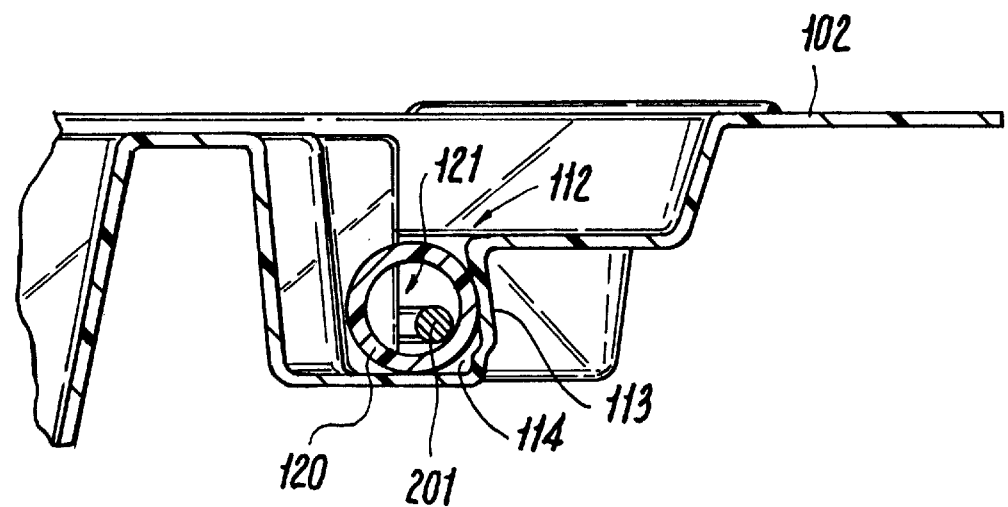

Referring to FIGS. 1, 2 and 3, second portion 112 is optionally semicircular in shape and preferably includes at least one, and preferably two or more, projection such as overhang flanges 113 which define an undercut region 114. Flanges 113 provide snap fit retaining means to releasably hold tube 120 in place within cavity second portion 112 of the depression. Flanges 113 can be formed as a shaped integral portion of the tray 102 during the thermoforming process.

Tube 120 is positioned in curved second portion 112 of the depression 110. As seen in FIG. 3, tube 120 is at least partially lodged in the undercut region 114 and is held in place by flanges 113, but can nevertheless be manually removed or inserted into said position and configuration.

Figure 4:
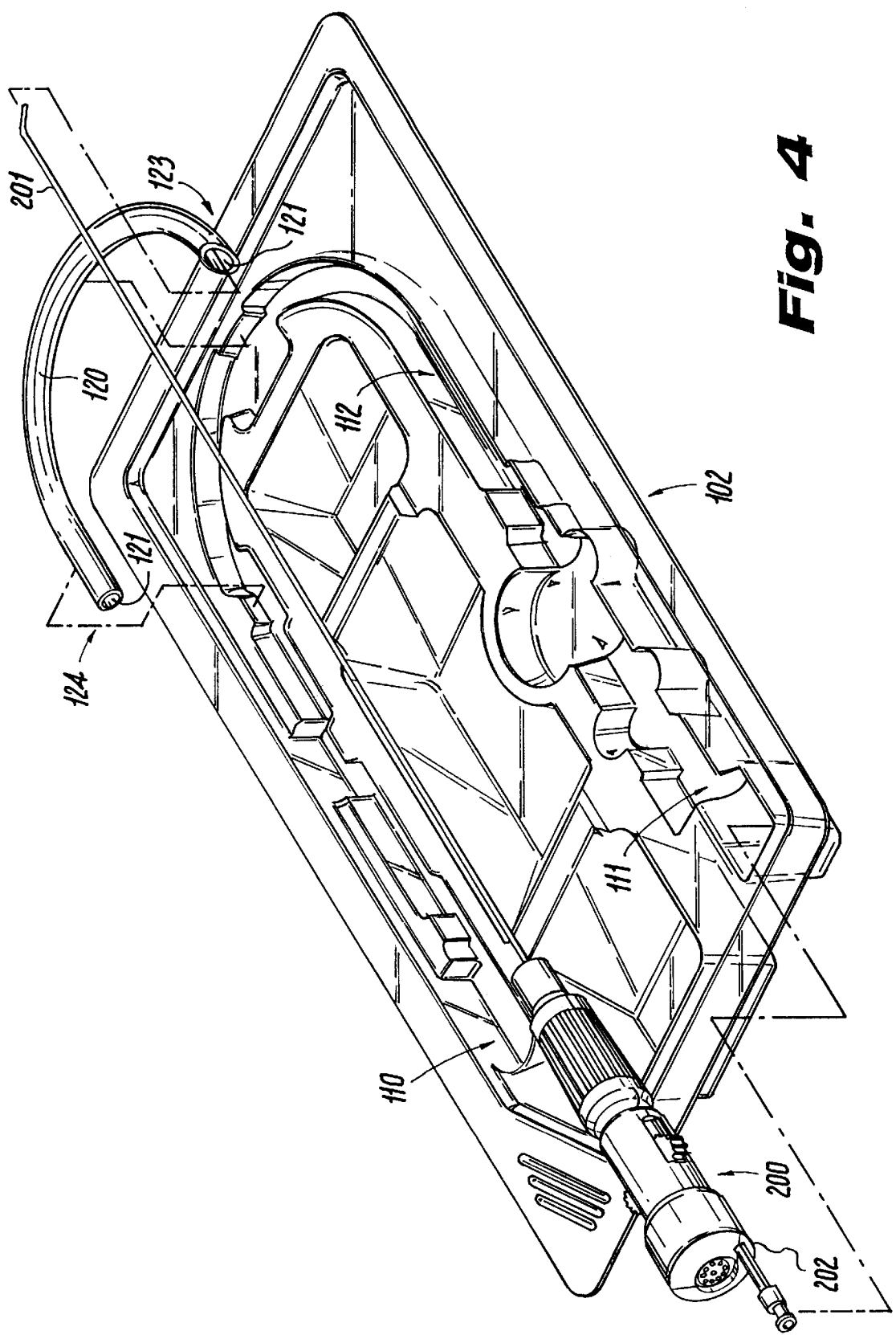
FIG. 4 is an exploded perspective view of the surgical instrument package and surgical instrument.

Referring to FIG. 4, to store the instrument 200, the flexible distal portion 201 is inserted into first end opening 123 and through bore 121 of the tube, and the tube is positioned in an arcuate configuration by snap fit engagement in second portion 112.

Figure 5:
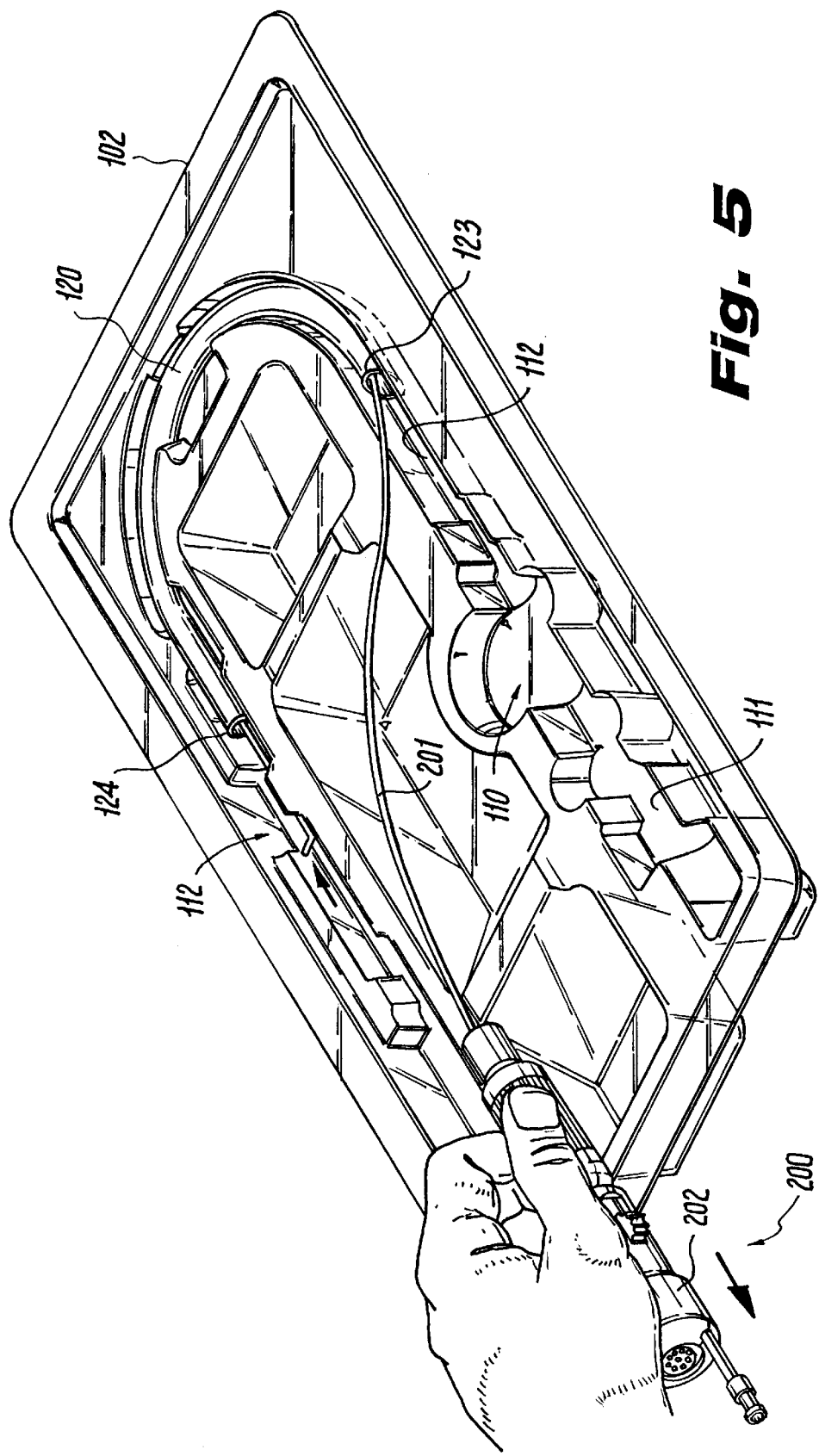
FIG. 5 is a perspective view showing removal of the surgical instrument.

Referring to FIG. 5, to remove the instrument 200 from tray 102 the body 202 is pulled so as to gradually withdraw distal portion 201 from tube 120 through first end opening 123. As the distal portion 201 withdraws it is straightened out. Thus, first end opening 123 serves as a single outlet through which the distal portion 201 exits the tube 120 in a controlled withdrawal. The distal portion 201 is not released in a lateral direction and therefore cannot suddenly spring from side to side until it is already straightened out. Therefore, tube 120 serves as a guide to limit withdrawal of the resiliently flexible distal portion 201 to movement in a direction substantially longitudinal with respect to the axis of the instrument 200.

Figure 6:
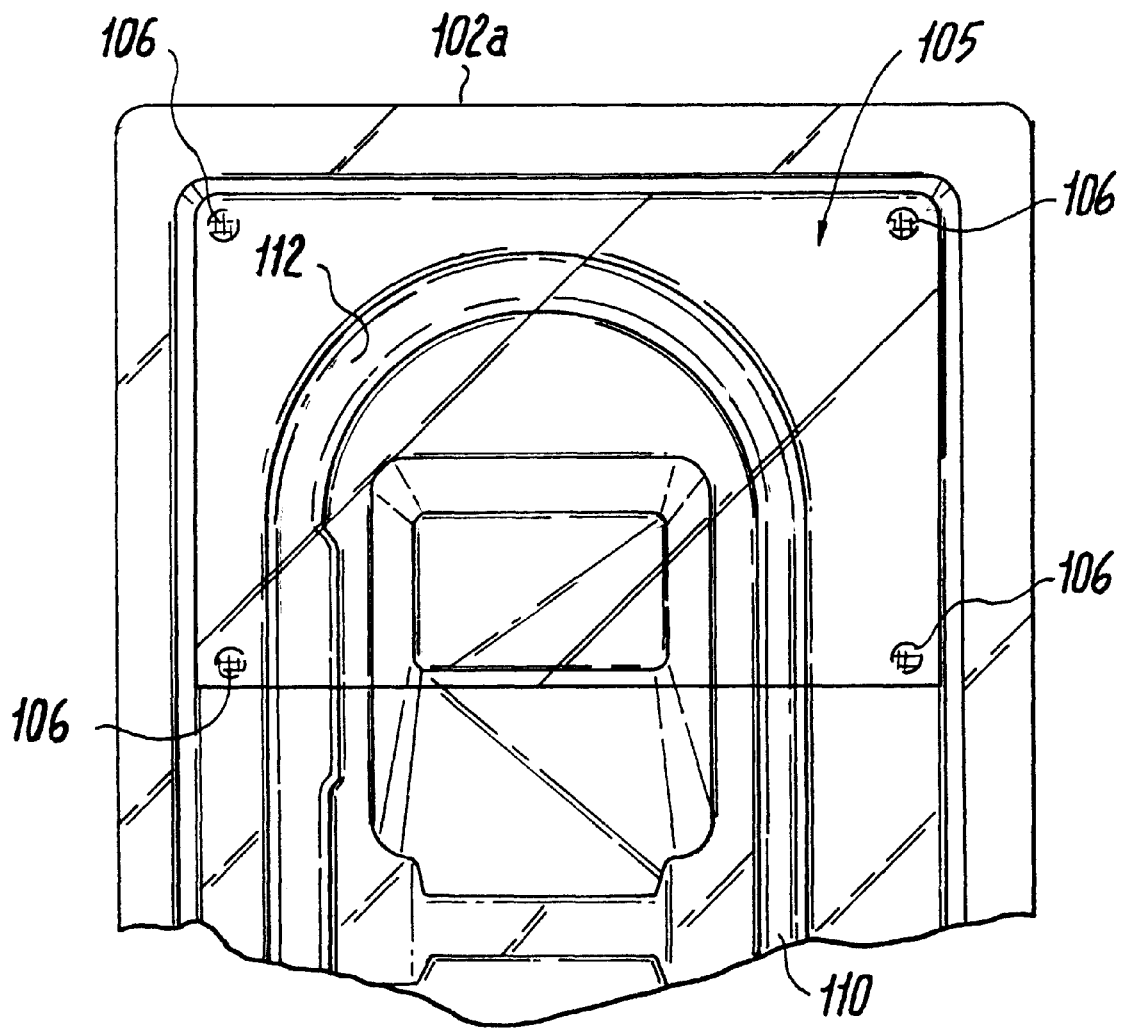
FIG. 6 is a plan view of an alternative embodiment of the surgical instrument package.

Referring to FIG. 6 an alternative embodiment 102a of the tray is similar to tray 102 in the material and method of fabrication but further includes a flap 105 which covers cavity second portion 112 and serves as a withdrawal limiting guide. Flap 105 is preferably fabricated from the same material as the tray 102a and is also preferably transparent. Alternatively, flap 105 can be fabricated from a sheet of spun bonded polyolefin fiber such as TYVEK® brand. Flap 105 prevents lateral withdrawal of the resiliently flexible distal portion 201 of the instrument from the narrow arcuate second portion 112 of the cavity 110, and limits withdrawal to a direction substantially longitudinal with respect to the axis of the instrument. Accordingly, use of a tube 120 is not required when flap 105 is employed, nor are the overhang flanges 113 and undercuts required to engage a tube. Flap 105 can be affixed to bottom portion 102 by means of spot welding at points 106, for example. Such spot welding can be done by heat, solvents, or adhesives. Alternatively, tray 102a and flap 105 can be snap fit together by means of snap-fit engageable bosses and concavities formed in the tray 102a and flap 105, for example at points 106.

It will be understood that various modifications may be made to the embodiments disclosed herein. Therefore, the above description should not be construed as limiting, but rather as exemplifications of preferred embodiments. Those skilled in the art will envision other modifications within the scope and spirit of the claims appended hereto.

What is claimed is:

1. A package for containing a medical instrument, the package comprising:

a) a tray with a storage space formed by a shaped cavity for holding the medical instrument, the storage space including a narrow arcuate portion of the shaped cavity;

b) a withdrawal guide associated with the tray, wherein the withdrawal guide comprises a guide tube having a longitudinal bore, the guide tube being engageable within the narrow arcuate portion of the shaped cavity, and wherein the narrow arcuate portion of the shaped cavity includes at least one curved wall having at least one projection with an undercut region for snap fit releasable engagement with the guide tube.

2. The package of claim 1 wherein the guide tube terminates at a first end and a second end said first end having an opening.

3. The package of claim 2 wherein said second end of the guide tube has an opening.

4. The package of claim 2 wherein said second end is closed.

5. The package of claim 2 wherein said first end is formed by an angled cut in the guide tube.

6. The package of claim 5 wherein said second end is formed by a cut perpendicular to the axis of the guide tube.

7. The package of claim 1 wherein the guide tube is fabricated from a flexible material.

8. The package of claim 1 wherein the guide tube is fabricated from a material selected from the group consisting of fluorocarbon polymer, polyvinyl chloride, polyethylene and nylon.

9. The package of claim 1 wherein the tray is fabricated from a transparent material.

10. The package of claim 9 wherein the tray is fabricated from a polymeric material selected from the group consisting of polyethylene terephthalate, polyvinyl chloride, polypropylene and polystyrene.

11. The package of claim 1 further including a cover attached to the tray.

12. The package of claim 11 wherein the cover is fabricated from a sheet of porous, microbe impervious material.

13. The package of claim 12 wherein the sheet of porous, microbe impervious material comprises a sheet of spun bonded polyolefin fiber.

14. The package of claim 1 wherein the storage space is defined by a depression in the tray.

15. A package for containing a medical instrument, the package comprising:
   a) a tray with a storage space formed by a shaped cavity for holding the medical instrument, the storage space including a narrow arcuate portion of the shaped cavity;
   b) a withdrawal guide associated with the tray,
   wherein the withdrawal guide comprises a flap attached to the tray and positioned over said narrow arcuate portion of the shaped cavity.

16. The package of claim 15 wherein said flap is spot welded to the tray.

17. The package of claim 15 wherein the flap is fabricated from a material selected from the group consisting of polyethylene terephthalate, polyvinyl chloride, polypropylene, polystyrene, and spun bonded polyolefin fiber.

18. The package of claim 15 wherein the flap is transparent.

19. The package of claim 15 wherein the flap is attached to the tray by means of corresponding engageable bosses and concavities.

* * * * *